United States Patent [19]

Smith

[11] Patent Number: 4,909,070
[45] Date of Patent: Mar. 20, 1990

[54] MOISTURE SENSOR

[76] Inventor: Jeffery B. Smith, 11 Milford St., East Victoria Park, Western Austrailia, Australia

[21] Appl. No.: 255,734

[22] Filed: Oct. 11, 1988

[30] Foreign Application Priority Data

Oct. 12, 1987 [AU] Australia ................ PI4818

[51] Int. Cl.⁴ .................................. G01R 27/26
[52] U.S. Cl. ........................ 73/73; 324/663; 324/690; 361/286
[58] Field of Search ........... 73/73, 336; 324/61 R, 324/61 P; 340/604, 605; 361/286

[56] References Cited

U.S. PATENT DOCUMENTS

| | | | |
|---|---|---|---|
| 2,304,448 | 12/1942 | Fletcher | 361/286 |
| 3,784,897 | 1/1974 | Norrie | 324/61 R |
| 3,803,570 | 4/1974 | Barlow et al. | 324/61 R |
| 3,860,918 | 1/1975 | Cencel | 324/61 R |
| 3,870,951 | 3/1975 | Brown et al. | 361/286 |
| 4,135,151 | 1/1979 | Rogers et al. | 324/61 R |
| 4,137,931 | 2/1979 | Hasenbeck | 73/73 |
| 4,168,466 | 9/1979 | Boldt | 324/61 R |
| 4,305,112 | 12/1981 | Heywang et al. | 361/286 |
| 4,482,581 | 11/1984 | Lorin et al. | 361/286 |
| 4,513,608 | 4/1985 | Cuming | 73/73 |
| 4,531,087 | 7/1985 | Larson | 73/73 |
| 4,546,645 | 10/1985 | Delmulle et al. | 73/74 |
| 4,583,399 | 4/1986 | Walsh et al. | 73/73 |
| 4,672,310 | 6/1987 | Sayed | 324/133 |

FOREIGN PATENT DOCUMENTS 8103709 12/1981 World Int. Prop. O. ......... 361/286

Primary Examiner—William A. Cuchlinski, Jr.
Assistant Examiner—Diego F. F. Gutierrez
Attorney, Agent, or Firm—Bachman & Lapointe

[57] ABSTRACT

A moisture sensor for detecting the moisture in a particulate material, the moisture sensor comprising a capacitance sensing probe having a first part with a dielectric coating and a second part, the second part being electrically conductive, physically isolated from the first part and disposed to be in electrical contact with the particulate material, and a capacitance detector connected to the first part and the second part, the capacitance detector being configured to generate an electrical signal dependant on the capacitance of the capacitance sensing probe. Soil moisture is measured by change in capacitance of the capacitance sensing probe.

13 Claims, 2 Drawing Sheets

MOISTURE SENSOR

The present invention relates to a moisture sensor particularly envisaged for use in detecting and measuring moisture in soil, although it is to be understood that it is of general applicability.

In general moisture sensors are in the form of conductivity/resistivity devices or soil suction/tension devices (tensiometers).

In the former case the sensor usually measures the conductivity of water in a gypsum block. Such measurement is very dependant on temperature and salts dissolved in the water (for example soil nutrients, fertilizers, and the like). Such sensors are also affected by variations in soil particle size and in the distribution of soil particle sizes, referred to as soil bulk density.

In the latter case the tensiometers are difficult to implement for automatic control of irrigation systems as they require frequent servicing to replenish a store of water used by the tensiometer. Also automatic type tensiometers are manufactured to a fixed soil suction and are not adjustable. Thus, different automatic type tensiometers are required for applications requiring different soil suctions.

The problems of the prior art sensors can be overcome by using a sensor which measures the change in the air void volume in soil as the volume of water in the soil changes. Surface tension of the water binds it to the soil causing air voids to open up in between the soil particles as the soil becomes less moist.

The soil moisture is sensed and measured by sensing and measuring the value of the capacitance between two plates of a capacitor. One plate of the capacitor is covered with a dielectric, such as PTFE, and the other plate is constituted by moist soil and air voids on contact with PTFE.

The amount of capacitance between the two plates varies as the amount of water in the voids immediately adjacent to the PTFE varies, since the variation in air volume that results with presence or absence of the water, is also a dielectric in the capacitance circuit.

Maximum capacitance occurs when the region between the two plates is saturated with water, leaving no voids, and as the void volume increases the capacitance decreases.

The present invention provides a moisture sensor to sense and/or measure the capacitance of a particulate substance having moisture.

In accordance with one aspect of the invention there is provided a moisture sensor for detecting the moisture in a particulate material, the moisture sensor comprising a capacitance sensing probe having a first part with a dielectric coating and a second part, the second part being electrically conductive, physically isolated from the first part and disposed to be in electrical contact with the particulate material, and a detection means connected to the first part and the second part, the detection means being configured to generate an electrical signal dependant on the capacitance of the capacitance sensing probe.

In accordance with another aspect of the present invention there is provided a capacitance sensing probe comprising a first part with a dielectric coating and a second part, the second part being electrically conductive, physically isolated from the first part and disposed to be in electrical contact with a particulate material in which the capacitance sensing probe is inserted.

Preferably, the dielectric coating is hydrophobic. The present invention will hereinafter be described with particular reference to use in detecting and measuring moisture in soil although it could be used with other particulate materials.

The present invention will now be described, by way of example, with reference to the accompanying drawings, in which.

Figure 1:
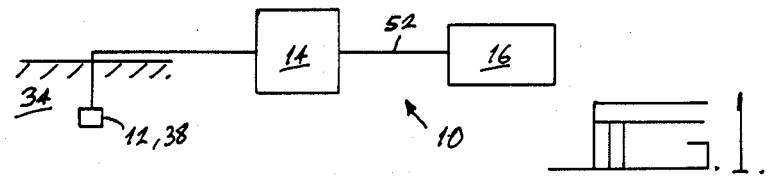
FIG. 1 is a schematic block representation of a moisture sensor in accordance with the present invention.
Figure 2:
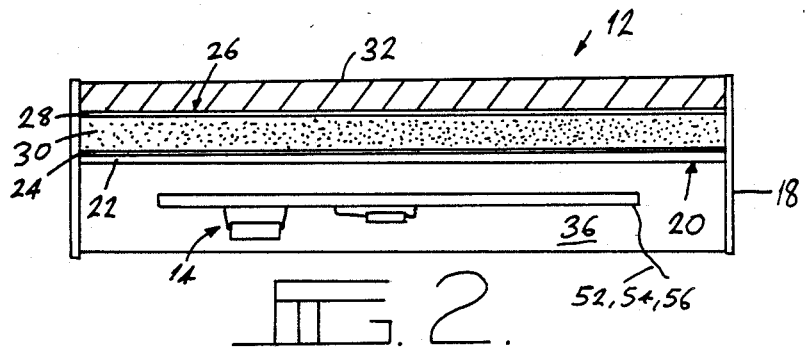
FIG. 2 is a cross sectional view of a capacitance sensing probe of the moisture sensor of FIG. 1.

In FIG. 1 there is shown a moisture sensor 10 comprising a capacitance sensing probe 12, a detection means, 14 electrically connected to the capacitance sensing probe 12 to detect a variation in the capacitance of the probe 12. The moisture sensor 10 may also comprise a measurement means 16 to measure the capacitance of the probe 12. As shown in the embodiment of FIG. 2, the probe 12 comprises a housing 18 having open ends and typically made of plastics materials. The probe 12 also comprises a first part 20 in the form of an electrically conductive plate 22 having a dielectric coating 24, such as PTFE, and is retained in the housing.

The probe 12 also comprises a second part 26 in the form of an electrically conductive mesh 28 retained in the housing 18. Preferably, the mesh is made from stainless steel. A layer of non-porous granular material 30, such as sand 30, is disposed between the plate 22 and the mesh 28. Preferably, the non-porous granular material is electrically insulative and hydrophilic. The sand comprises grains of particles having a graded distribution of sizes. The layer of sand is typically between 0.5 to 5 mm thick, more particularly between 1 to 2.5 mm thick. The probe 12 also comprises a layer of porous material 32 such as ceramic or gypsum located adjacent to the mesh 28 and opposite the layer of sand 30. The porous material 32 preferably has a particle size smaller then most soils so that the sand in the layer of sand 30 and the sand in soil 34 in which the sensor 10 is located in use, tends not to enter into the porous layer 32 or render it non-porous. Preferably, the thickness of the sand 30 and the porous layer 32 is relatively small such as less than about 10 mm, more preferably 1 to 4 mm. Preferably, the porous layer 32 is made of ceramic since it is harder wearing than gypsum. It is envisaged that the layer of sand 30 could be replaced with other non-porous, insulating paticulate materials, such as glass beads or the like.

Preferably, the housing 18 comprises a void behind the plate 22 to receive the detection means 14. Typically, the detection means 14 is encapsulated in epoxy resin 36 in the void.

It is envisaged that the first part 20 could be in the form of a wire coated with a dielectric and stationed in the layer of sand 30 between the mesh 28 and the epoxy resin 36.

It is also envisaged that the first part 20, second part 26 and the layer of porous material 32 could be co-axially arranged cylinders having a housing 18 in the form of two end cups and with the detection means 14 located inside a void created by the first part 20.

Preferably, the thickness of the layers 30 and 32 is kept small to allow for rapid passage of moisture as described hereinafter.

Figure 3A:
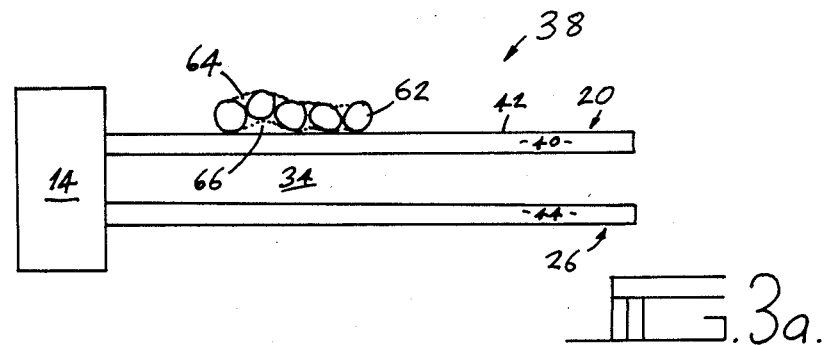
FIGS. 3a and 3b are cross sectional views of two other embodiments of a capacitance probe of the moisture sensor of FIG. 1.

In FIG. 3a there is shown another embodiment of a sensing probe 38, like numerals denoting like parts, in which the first part 20 is in the form of a rod 40 having an encapsulating dielectric coating 42, such as, PTFE. Preferably, the coatings 24 and 42 are made of material which is hydrophobic to inhibit the formation of a film of water on the surface of the sensing probes 12 and 38. The rod 40 has a cross sectional dimension of between 1 mm to 25 mm although other sizes may be useful.

Figure 3B:
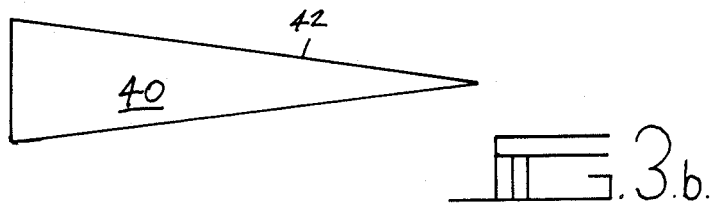

The rod 40 could be tapered such as in the shape of a cone as shown in FIG. 3b. Such shape enables substantially equal contact force with depth of placement into the soil 34 to achieve a substantially uniform contact pressure between the soil and the sensing probe 12.

The rod 40 is conveniently between 10 cm and 100 cm in length, such as, for example, between 15 to 20 cm. The probe 38 also comprises a ground member 44 arranged for electrical contact with the soil 34 adjacent the rod 40. The ground member 44 may be in the shape of a flat plane or a bar or the like. The ground member 44 is made of electrically conductive metal materials, such as stainless steel. Preferably, the ground member 44 has a relatively large surface area to provide good electrical contact to the soil 34.

The rod 40 is electrically isolated from the ground member 44 by the coating 42.

Figure 4:
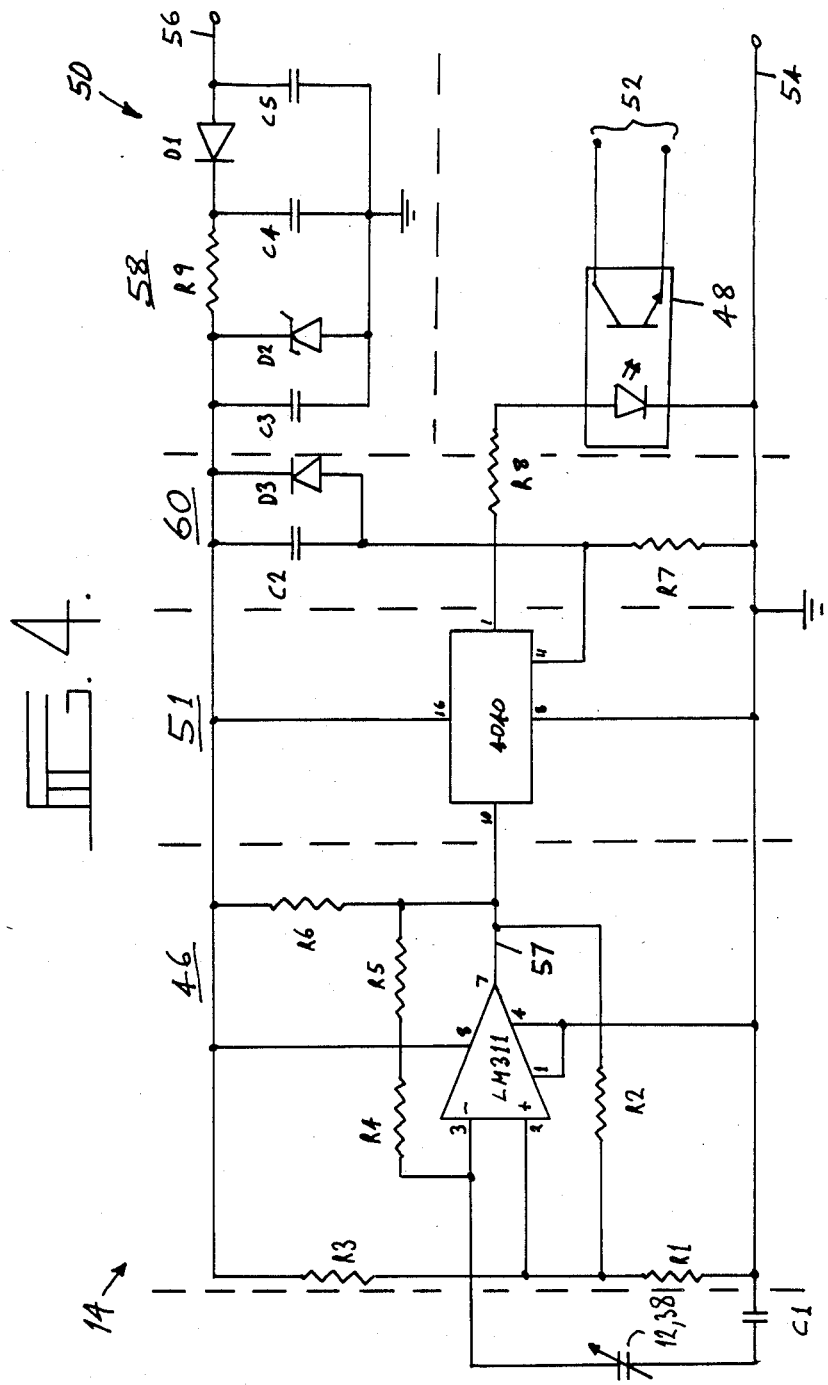
FIG. 4 is an electrical circuit of a detection means of the moisture means of FIG. 1.

The detection means 14 is shown in FIG. 4 and comprises a precision RC oscillator 46, an opto coupler 48 driven by the RC oscillator 46 and a power supply 50. A frequency divider 51 may be located between the RC oscillator 46 and the opto coupler 48. The divider 51 may typically have a division of about 16000. The divider 51 is intended to reduce the frequency of the oscillator 46 to a frequency which can readily be conducted over a low quality electrical cable.

The opto coupler 48 is connected to an electrical cable 52 conventionally used in reticulation systems. An opto coupler 48 is preferred so as to isolate the signal from the detection means 14 from the second part 26, 28, 44 of the sensor 12, 38 to inhibit electrical earth loops that may cause electrolysis of components.

For this reason a capacitor C1 is connected between the second part 26, 28, 44 and a low potential supply rail 54 of the detection means 14.

Typically, the RC oscillator 46 comprises an LM311 opamp with feed back resistors R4 and R5, to provide a capacitor changing source for the opamp. Resistor R5 provides temperature compensation for the LM311 and is prefererably a carbon composition resistor. The RC oscillator 46 has comparator switching levels set by resistors R1 to R3. The capacitor for the RC oscillator 46 is provided by the sensing probe 12, 38 which is connected to an inverting input 3 of the LM311.

Typically, the resistors R1 to R3 are of equal value and about 100 kohms to provide ⅓ and ⅔ of the supply voltage (here set by zener diode D2 to about 5.6 volts) from a high potential supply rail 56.

The frequency of oscillation of the RC oscillator is dependent on the capacitance of the sensing probe 12, 38 and the resistors R4 to R6 and is typically in the range from 80 to 800 Khz. The RC oscillator has an output 57 which is substantially a square wave voltage waveform in this range of frequencies.

Typically, the resistors R4 to R6 are valued 82 kohms, 18 kohms and 8.2 kohms respectively.

Preferably, the RC oscillator 46 has a relatively high input resistance so as to reduce variations in capacitance measurement due to variations in conductivity of the soil 34.

The detection means 14 also comprises a regulator 58 having a spike suppression capacitor C5, halfwave rectifier diode D1, a filter arrangement formed of capacitors C3 and C4, a resistor R9, and the zener diode D2.

The detection means 14 also comprises a delay circuit 60 formed of a capacitor C2, a resistor R7 and a diode D3. The delay circuit 60 causes a delay in output from the opto coupler 48 after application of power to the detection means 14 for a period of about 10 seconds.

When the moisture sensor 10 is used with a reticulation system the delay is used by the measuring means 16 to detect when the reticulation system changes watering cycles by activating another reticulation control valve of the reticulation system. This activation also activates the detection means 14 associated with the control valve as described hereinafter. The delay prevents output to the cable 52 immediately after activation and so the measuring means 16 detects a pause in signals of say 10 seconds in change over from one metering cycle to the next.

It has been found that the soil capacitance change from dry to saturated soil is relatively small. Accordingly, the detection means 14 preferably is configured to operate to resolve such small changes in capacitance. For example, in the embodiment of FIG. 2 the capacitance may change from 50 pf to 300 pf, for dry soil through to saturated soil and for the embodiment of FIG. 3a, the change could be from 2 pf to 5 pf.

The measurement means 16 is configured to measure a characteristic, such as, the period or the voltage or frequency of a signal eminating from the opto coupler, the signal being proportional to the change in capacitance of the probe 12, 38. The measurement means 16 may then determine the correct moisture content of the soil 34. It has been found preferable to measure the changes in period of the output of the RC oscillator as such gives results substantially proportional to the capacitance of the sensing probes 12, 38 and hence the moisture. Also period data is generally less corrupted over the cable 52, which cable 52 is generally of a low quality. Further, period measurements can be done more quickly and easily than frequency measurements. Voltage data is suitable only over relatively short lengths of cable.

It is preferred that the said means 16 be encapsulated in resin or the like to insulate it from ambient temperatures and humidity.

The sensing probe 12 of the first embodiment is most preferred since it has greater readings in capacitance and hence greater accuracy and resolution in measuring soil moisture. Also due to the use of a layer of graded sand 30 the sensing probe 12 is less prone to variation in bulk density of the soil 34 and so is easier and more accurately installable into the soil 34. The embodiments of FIGS. 3a and 3b in contrast, must preferably, be installed into saturated soil 34 to give a maximum moisture reading. Also the former embodiment is less effected by root activity in its proximity. In the latter embodiments this can lead to creation of air gaps adjacent the rod 40 which bias the moisture reading.

In use, the sensing probe 12, 38 is inserted into the soil 34 whose moisture is to be measured. Preferably porous material 32 is disposed upright, more preferably vertically so that the probe 12 doesn't collect a pool of water. The plate 22 or rod 40 is electrically connected to input 3 of the opamp LM311 of the oscillator 46 and the mesh 28 or ground member 44 is electrically connected to the capacitor C1.

The opto coupler 48 is then connected to the cable 52 and thereby to the measuring means 16. The supply rails 54 and 56 are conveniently connected to a 24 volt AC supply used to power reticulation control valves.

Moisture in the soil 34 is absorbed by the porous material 32 since it is dryer than the soil 34. Similarly, the moisture from the porous material 32 is absorbed into the layer of sand 30. This suction/tension reaction takes place until hydrostatic balance is achieved between the soil 34, the porous material 32 and the sand 30.

As typified in FIGS. 3a soil/sand particles 62 have water 64 formed between them and voids of air 66 generated adjacent the first part 20.

As the sand 30 becomes more moist the volume and number of the voids 66 decreases and raises the capacitance of the sensing prove 12 towards its maximum set by the coating 24. As the sand 30 becomes less moist the volume and number of voids 66 increases and decreases the capacitance of the sensing probe 12.

The changes in capacitance of the soil 34 to the coating 24 causes the RC oscillator 46 to oscillate at a different frequency and hence the period of the oscillation is altered. It has been found that the change in period is substantially proportional to the changes in capacitance and hence moisture.

By use of the moisture sensor 10 of the present invention the moisture of soil 34 or the like may be rapidly measured and the measurement being substantially independent of temperature, soil particle size, and bulk density soil salinity and soil pH.

Since the measurement is relatively rapid the moisture sensor 10 may be coupled to an automatic irrigation control system to activate same when the soil moisture falls below a set moisture and to deactivate same when the soil moisture exceeds a set moisture.

Also the moisture at which the activation and deactivation occur may be altered to allow for the requirements of particular soil types and particular plants.

The rapid measurement enables the sensor 10 to detect the wetting front created when water is applied from the irrigation system.

Also, since the sensor 10 relies on measured capacitance there can be electrical isolation between the plurality of the sensors 10 located about an area to be irrigated. Whereas prior art resistive sensors are plaugued by electrical interaction between a plurality of the sensors. It is also envisaged that the sensors 10 could be located at different depths to give readings of moisture with soil depth.

The electrically conductive plate 22, the wire or the rod 40 constitute an electrically conductive means.

The precision RC oscillator 46 constitutes a capacitance sensitive means.

The low potential supply rail 54 constitutes a ground potential connection.

Modifications and variations such as would be apparent to a skilled addressee are deemed within the scope of the present invention.

I claim:

1. A capacitance sensing probe for sensing changes in moisture in a particulate material, the capacitance sensing probe comprising:

(a) a capacitance sensing probe having a first part and a second part located adjacent the first part;

(b) the first part having a hydrophobic dielectric coating and an electrically conductive means covered thereby and being disposed so that the dielectric coating is in physical contact with the moisture in the particulate material;

(c) the dielectric coating having voids adjacent it and allowing moisture to move in and out of the voids dependant on the moisture of the particulate material; and (d) the second part being electrically conductive and disposed for electrical contact with the moisture in the particulate material, whereby the dielectric coating and the voids constitute a capacitance whose value is dependant on the moisture in the particulate material, and the electrically conductive means and the moisture in the particulate material constitute electrical conductors for the capacitance.

2. A capacitance sensing probe according to claim 1, in which:

the electrically conductive means is a plate and the second part is an electrically conductive mesh;

the capacitance sensing probe further comprising a housing for the plate and the mesh and a layer of non-porous granular material having a graded distribution of particle sizes;

the non-porous granular material being electrically insulative and hydrophilic and being confined between the dielectric coating and the mesh; and a layer of porous material adjacent the mesh opposite the non-porous granular material, the layer of porous material being disposed to be in contact with the particulate material in use.

3. A capacitance sensing probe according to claim 1, in which:

the electrically conductive means is a rod and the second part is an electrically conductive ground member; and the rod is tapered toward one end to enable substantially equal contact force with depth of placement on the first part into the particulate material.

4. A capacitance sensing probe according to claim 1, in which:

the electrically conductive means is a plate, the second part is an electrically conductive mesh, and the capacitance sensing probe further comprises a housing for the plate and the mesh and a layer of non-porous granular material having a graded distribution of particle sizes;

the non-porous granular material being electrically insulative and hydrophilic and being confined between the plate and the mesh; and a layer of porous material adjacent the mesh opposite the non-porous granular material, the layer of porous material being disposed to be in contact with the particulate material in use.

5. A moisture sensor for detecting the moisture in a particulate material whose moisture is to be sensed, the moisture sensor comprising:

(a) a capacitance sensing probe having a first part and a second part located adjacent the first part;

(b) the first part having a hydrophobic dielectric coating and an electrically conductive means covered thereby, the first part being disposed so that the dielectric coating is in physical contact with the moisture in the particulate material, the dielectric coating having voids adjacent it and allowing moisture to move in and out of the voids dependant on the moisture of the particulate material;
(c) the second part being electrically conductive and disposed for electrical contact with the particulate material;
(d) the dielectric coating and the voids constituting a capacitance whose value is dependant on the moisture in the particulate material, and the electrically conductive means and the moisture in the particulate material constituting electrical conductors for the capacitance; and
(e) a detection means comprising a capacitance sensitive means electrically connected to the electrically conductive means of the first part and a ground potential connection connected to the second part, the detection means generating an electrical signal dependant on the capacitance of the capacitance sensing probe when disposed in the moist particulate material.

6. A moisture sensor according to claim 5, in which: the capacitance sensitive means is an RC oscillator whose frequency of oscillation is dependant on the capacitance of the capacitance sensing probe; and the detection means further comprises a capacitor to AC couple the capacitance sensing probe to the RC oscillator and an opto coupler driven by the RC oscillator and having an output carrying an electrical signal which is dependant on the capacitance of the capacitance sensing probe.

7. A moisture sensor according to claim 6, in which a frequency divider is disposed between the RC oscillator and the opto coupler.

8. A moisture sensor according to claim 6, in which the RC oscillator comprises a carbon composition resistor in a feed back network to compensate for temperature dependencies of the RC oscillator.

9. A moisture sensor according to claim 6, comprising a measurement means connected to the output of the opto coupler by a cable, the measurement means being configured to measure the electrical signal at the output of the opto coupler.

10. A moisture sensor according to claim 6, comprising a measurement means connected to the output of the opto coupler by a cable, the measurement means being configured to measure the period of the electrical signal at the output of the opto coupler.

11. A moisture sensor according to claim 6, comprising a measurement means connected to the output of the opto coupler by a cable, the measurement means being configured to measure the frequency of the electrical signal at the output of the opto coupler.

12. A moisture sensor according to claim 6, in which:
the electrically conductive means is a rod and the second part is an electrically conductive ground member; and
the rod being tapered toward one end to enable substantially equal contact force with depth of placement of the first part into the particulate material.

13. A moisture sensor according to claim 6, in which:
the electrically conductive means is a plate, the second part is an electrically conductive mesh and the capacitance sensing probe further comprises a housing for the plate and the mesh and a layer of non-porous granular material having a graded distribution of particle sizes;
the non-porous granular material being electrically insulative and hydrophilic and being confined between the dielectric coating and the mesh; and
a layer of porous material adjacent the mesh opposite the non-porous granular material, the layer of porous material being disposed so as to be in contact with the particulate material in use.

* * * * *